United States Patent
Kelm et al.

(10) Patent No.: US 7,820,714 B2
(45) Date of Patent: Oct. 26, 2010

(54) SIGLEC INHIBITORS

(76) Inventors: Sorge Kelm, Am Saatmoor 25 a, Lilienthal (DE) 28865; Reinhard Brossmer, Kurt-Lindemann-Strasse 21, Neckargemund (DE) 69151

( * ) Notice: Subject to any disclaimer, the term of this patent is extended or adjusted under 35 U.S.C. 154(b) by 817 days.

(21) Appl. No.: 10/481,529

(22) PCT Filed: Jun. 7, 2002

(86) PCT No.: PCT/EP02/06277

§ 371 (c)(1),
(2), (4) Date: Feb. 13, 2004

(87) PCT Pub. No.: WO03/000709

PCT Pub. Date: Jan. 3, 2003

(65) Prior Publication Data

US 2004/0176309 A1    Sep. 9, 2004

(30) Foreign Application Priority Data

Jun. 19, 2001 (DE) .................. 101 29 332
Apr. 12, 2002 (DE) .................. 102 16 310

(51) Int. Cl.
*A61K 31/35* (2006.01)
*C07D 315/00* (2006.01)
(52) U.S. Cl. .......... 514/459; 514/23; 549/419
(58) Field of Classification Search .......... 536/108; 514/23, 459; 549/419
See application file for complete search history.

(56) References Cited

FOREIGN PATENT DOCUMENTS

WO    WO 92/22301 A1    12/1992

OTHER PUBLICATIONS

Crocker et al., "Siglecs: A Family of Sialic-acid Binding Lectins," *Glycobiology*, 8(2): v-vi (1998).
Crocker et al., "The Siglec Family of I-Type Lectins," *Carbohydrates in Chemistry and Biology*, Ernst et al. (Ed.) (Wiley-VCH, Weinheim) 4: 579-595 (2000).
Crocker et al., "Siglecs in the Immune System," *Immunology*, 103: 137-145 (2001).
Kelm, "Ligands for Siglecs," *Mammalian Carbohydrate Recognition Systems*, P.R. Crocker (Ed.) (Springer, Berlin ) 153-176 (2001).
Li et al., "Cloning and Characterization of Siglec-10, a Novel Sialic Acid Binding Member of the Ig Superfamily, from Human Dendritic Cells," *J. Biol. Chem.*, 276(30): 28106-28112 (2001).
May et al., "Crystal Structure of the N-Terminal Domain of Sialoadhesin in Complex with 3' Sialyllactose at 1.85 Å Resolution," *Molecular Cell*, 1: 719-728 (1998).
Strenge et al., "Glycan Specificity of Myelin-associated Glycoprotein and Sialoadhesin Deduced from Interactions with Synthetic Oligosaccharides," *Eur. J. Biochem.*, 258: 677-685 (1998).
Kelm et al., "Functional Groups of Sialic Acids Involved in Binding to Siglecs (sialoadhesins) Deduced From Interactions with Synthetic Analogues," *Eur. J. Biochem.*, 255: 663-672 (1990).
Kelm et al., "The Ligand-binding Domain of CD22 is Needed for Inhibition of the B Cell Receptor Signal, as Demonstrated by a Novel Human CD22-specific Inhibitor Compound," *J. Exp. Med.*, 195(9): 1207-1213 (2002).
Mirelis et al., "Photoreactive CMP-Sialic Acids as Substrates for α2,6-Sialyltransferase," *Bioorganic & Medicinal Chemistry Letters*, 5(23): 2809-2814 (1995).
Murakami et al., "Chemoenzymatic Synthesis of Neuraminic Acid Analogs Structurally Varied at C-5 and C-9 as Potential Inhibitors of the Sialidase from Influenza Virus," *Carbohydrate Research*, 280: 101-110 (1996).
Norton et al., "The Sythesis of C-9 Modified Derivatives of the α-Methyl Glycoside of KDN Methyl Ester," *J Carbohydrate Chemistry*, 20(2): 227-238 (2001).
Troncoso et al., "Specificity of the Binding Site of the Sialic Acid-binding Lectin from Ovine Placenta, Deduced from Interactions with Synthetic Analogues," *Glycoconjugate Journal*, 17: 705-711 (2000).
Ogawa et al., "Synthesis of carbocylic analogues of 3-deoxy-D-*manno*-2-octulosonic acid and *N*-acetylneuraminic acid", *Carbohydrate Research* 269, pp. 53-78 (1995).
Sparks et al., "Neuraminidase-Resistant Hemagglutination Inhibitors: Acrylamide Copolymers Containing a C-Glycoside of *N*-Acetylneuraminic Acid", *J. Med. Chem.* 36, pp. 778-783 (1993).

*Primary Examiner*—Taylor Victor Oh
(74) *Attorney, Agent, or Firm*—Leydig, Voit & Mayer, Ltd.

(57) ABSTRACT

The invention relates to Siglec inhibitors that have an increased affinity for the receptor molecule. The Siglec inhibitors provided by the invention are preferably selective of a given Siglec molecule. The invention further relates to a method for producing Siglec inhibitors and to a method for increasing the binding selectivity for a given Siglec molecule. The invention also relates to pharmaceutical compositions that contain the Siglec inhibitors and to medical indications for the Siglec inhibitors.

2 Claims, No Drawings

SIGLEC INHIBITORS

This application is the U.S. national phase of international patent application PCT/EP02/06277, filed on Jun. 7, 2002, and claiming priority to German patent application nos. 10129332.1, filed Jun. 19, 2001, and 10216310.3, filed Apr. 12, 2002, all of which are hereby incorporated by reference.

The invention relates to siglec inhibitors and pharmaceutical compositions which contain them. Furthermore, the invention relates to methods of increasing the binding selectivity of siglec inhibitors and specification of the medical indications of the siglec inhibitors provided.

Siglecs (sialic acid binding Ig-like lectins) are Ig-type lectins which are characterised by an N-terminal V-set domain which mediates the sialic acid bond. A varying number of Ig domains of the C2 set follows the Ig domain. Originally, the lectin family was found based on independent studies of sialoadhesin (siglec-1 CD 169), a macrophage lectin-like adhesion molecule and CD22 (siglec-2), a B-cell restricted member of the Ig superfamily (IgSF), which plays an important role in the regulation of the B-cell activation. It was also found that both molecules mediate the cell-cell interactions in vitro by the detection of sialylated glycoconjugates. The cloning of sialoadhesin indicated high sequence similarities to CD22 and led to the conclusion that two further IgSF proteins, having a relationship in this respect, the myelin-associated glycoprotein (MAG/siglec-4) and CD33 (siglec-3), the binding of which to sialic acid was not previously known, also represent members of the siglec family. Six other human siglec molecules (siglecs 5-10) have been identified and characterised. These previously unknown molecules exhibit a high degree of sequence similarity to CD33 in their extracellular and intracellular domains and are collectively termed "siglecs standing in relation to CD33" (1; summary article). Reference (7) describes the cloning and characterisation of siglec-11 which is expressed from human dendritic cells.

Table 1 gives an overview of the occurrence and potential functions of the previously described siglecs.

TABLE 1

Occurrence and potential functions of the previously described siglecs

| Name | Occurrence | Potential function |
| --- | --- | --- |
| Sialoadhesin (Sn, siglec-1) | Macrophage subpopulations | Cellular interactions of macrophages |
| CD22 (siglec-2) | B-lymphocytes | Modulation of the B-cell dependent immune response; homing in bone marrow |
| CD33 (siglec-4) | Myeloid precursor cells | Unknown |
| Myelin-associated glycoprotein (MAG, siglec-4a): Schwann cells myelin protein (SMP, siglec-4b) | Myelinated cells of the central and peripheral nervous system (oligodendrocytes and Schwann cells) | Receives the myelin structure and function; regulation of the neurite growth |
| OB-BP2 (siglec-5) | Neutrophile granulocytes, monocytes | Unknown; presumably signal transduction |
| OB-BP1 (siglec-6) | Placenta (cyto- and syncytiotrophoblasts); B-lymphocytes | High affinity leptin bond independent of Sia; function of the Sia bond unknown |
| p75 / AIRM1 (siglec-7) | Natural killer cells | Inhibitory receptor of natural killer cells |
| Siglec-8 | Eosinophilic granulocytes | Unknown; presumably signal transduction |

TABLE 1-continued

Occurrence and potential functions of the previously described siglecs

| Name | Occurrence | Potential function |
| --- | --- | --- |
| Siglec-9 | Monocytes; neutrophilic granulocytes; CD16$^+$ CD56$^-$ cells | Unknown; presumably signal transduction |
| Siglec-10 | B-cells, monocytes and other leucocytes | Unknown; presumably signal transduction |
| Siglec-11 | Dendritic cells, monocytes and other leukocytes | Cellular recognition; signal transduction |

As can be seen from the table, siglecs also participate in the reduction of the immune response, the maintenance of the organisation of myelin in the nervous system and in the hematopoesis.

The interactions mediated by siglecs may be of two types. Firstly, signals in the cells which express the corresponding siglec can be produced by binding of the siglec molecules (e.g. damping of the B-cell dependent immune response, inhibition of the cytotoxic activity of natural killer cells (NK cells) by phosphorylation of ITIM motives), or signals can be produced at the cell bound by the siglec (e.g. regulation of the neurite growth of neurons by siglec-4a, [MAG] (1, 2)).

The effect of the binding partners of the siglecs can occur here in two ways (3). Firstly, monovalent substances can impair the biologically relevant cross-linking of the siglec molecules to each other or impair it with other molecules. This would lead to a reduction of the signal. Secondly, polyvalent substances can reinforce the triggered signal. Consequently, a regulation in both directions is possible. Suitable specific substances are required for these processes.

Sialic acid is a generic term for a large family of 9-carbon atom sugars which represent all the derivatives of neuraminic acid (Neu) or keto-desoxy-nonulsonic acid (KDN). Typically these are found on the exposed non-reducing ends of the oligosaccharide chains which are linked to a large number of proteins and lipids.

The sialic acid binding site of the siglec lies in the N-terminal domain which is a V-set domain and which contains characteristic structural features for siglecs. The position of the binding site and the amino acids participating in the binding were found by X-ray structural analysis of co-crystals of siglec-1 (sialoadhesin) and 2,3-sialyllactose. The contributions of the functional groups of sialic acid to the binding were determined from Hapten inhibition experiments with synthetic sialic acid derivatives (5, 6). Summarizing, these studies have shown that, among other aspects, the hydroxyl group on the C-9 of the sialic acid provides a substantial contribution as a hydrogen donor in a hydrogen bridge for binding and can be substituted by an amino group (5).

To regulate the biological functions mediated by siglecs, binding partners are required which occupy the binding sites with high affinity.

It is therefore the object of this invention to provide siglec inhibitors with a high affinity. A preferred object is the provision of siglec inhibitors with increased affinity which bind as specifically as possible to single siglec receptors.

The object of this invention is solved by the provision of siglec inhibitors with the formula:

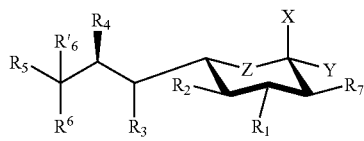

whereby
- X signifies a negatively charged group such as a carboxy, phosphate or sulphate group or a derivative of them;
- Y signifies an H atom, an alkyl or aryl group, a hydroxy group, a glycan, a polymer carrier molecule or a derivative of them;
- Z is selected from O, N, C and S;
- R1 signifies an H atom, a hydroxy group or a derivative of them;
- R2 signifies a hydroxy or amino group or a derivative of them;
- R3 signifies a hydroxy group or a derivative of it;
- R4 signifies a hydroxy group or a derivative of it;
- R5 signifies a substituted or unsubstituted amino group, whereby the substituent is selected from
- a substituted or unsubstituted formyl, alkanoyl, cycloalkanoyl, aryl-carbonyl, heteroaryl-carbonyl, alkyl, aryl, cycloalkyl or heteroaryl group, whereby these residues can also include one or more unsaturated bonds,
- whereby R4 acts as H acceptor and R5 as H donor;
- R6 signifies an H atom or an alkyl group, a charged group or a derivative of them;
- R6' signifies an H atom or an alkyl group, a charged group or a derivative of them, whereby at least one substituent is selected from R6 and R6' is a hydrophobic group, preferably an H atom or a methyl group; and
- R7 signifies an H atom or any group, preferably a group for improving the pharmacological properties of the siglec inhibitor.

In the following some terms are defined as they are taken in relation to this application.

The term "siglec" includes all siglec molecules. Reference should be made to (8) for the definition of a siglec molecule. The amino acid sequences of the siglec molecules siglec-1 to siglec-10 can, for example, be taken from the references listed in (1, Table 1). The amino acid sequence of siglec-11 can be taken from (7). The amino acid sequences of the siglec molecules can also be obtained from the publicly accessible data base, Entrez (internet address: www.ncbi.nlm.nih.gov./entrez). The siglec molecules can in this respect be present in their natural environment on naturally occurring cells or in artificial environments.

The term "siglec inhibitor" generally signifies the capability of a compound to inhibit the binding of a sialic acid molecule, in particular the natural ligand, to the siglec protein. A siglec inhibitor according to the invention activates or deactivates a given siglec protein depending on its structure. Preferably, the reference compound of the sialic acid is methly-α-5'-N-acetyl-neuraminic acid. Preferably, the inhibition can be determined by a Hapten inhibition test. The Hapten inhibition test is here based on Fc-chimeras which consist of N-terminal domains of siglecs and the Fc part of the human IgG, complexed with radioactively marked anti-Fc antibodies and incubated with various concentrations of the potential inhibitors to be investigated, before suitable target cells, preferably human erythrocytes, are added. After overnight incubation at 4° C. the unbound complexes are removed by washing the cells and the bound radioactivity is determined. From the data obtained in this way, the concentrations are found which lead to 50% inhibition of the binding (IC50 values) (5, 6). Specially preferred during the Hapten inhibition test was 10 μl of the complex solution with an activity of $10^3$ Bq $^{125}$I mixed with the same volume of a solution of the substance to be investigated (concentrated three times) and incubated at 4° C. for one hour. Then followed the addition of 10 μl of a suspension of target cells, preferably 0.25 to 0.5% of human erythrocytes and incubation overnight at 4° C. The unbound radioactivity is removed by washing the cells five times with 200 μl of washing buffer, preferably phosphate-buffered saline with 0.1% (W/V) bovine serum albumin, and the cell-bound activity is determined with a γ-counter. As a control, preferably the binding of sialidase-treated cells and of untreated cells is measured without the substance to be investigated. The inhibition is determined in that the value without inhibitor is set to 0% and that with the sialidase-treated cells is set equal to 100%.

The term "derivative" generally means in relation to the residues X, Y, R1-R4, that the group occurring in the neuraminic acid is substituted by a bioisosteric group, which exhibits essentially the same biological activity. The concept of bioisosterics is known to the specialist.

The expression "a substituted formyl, alkanoyl, cycloalkanoyl, aryl-carbonyl, heteroaryl-carbonyl, alkyl, cycloalkyl or heteroaryl group" means that the relevant groups exhibit substituents which leave the biological properties essentially unmodified. This includes, for example, low-alkyl substituents, such as for example methyl, ethyl, propyl and butyl groups.

According to the invention, X signifies a negatively charged group. This negatively charged group presumably forms a salt bridge with an arginine residue of the siglec receptor. The naturally occurring substituent is a carboxy group. Suitable derivatives of it are, for example, a phosphate or sulphate group. Furthermore, phosphonate and sulphonate groups are also taken into account. Other suitable derivatives are a carboxy methylene or carboxy ethylene group.

According to the invention, Y signifies an H atom, an alkyl or aryl group, a hydroxy group, a glycan, a polymer carrier molecule or a derivative of them. The naturally occurring substituent is a hydroxy group. Suitable derivatives of the hydroxy group are in this respect an amino or thio group. Suitable glycans are in this respect hexoses, hexosamines and/or pentoses or derivatives of them, preferably glucose or galactose or derivatives of them. Furthermore suitable glycans are oligo and polysaccharides, whereby the oligo and polysaccharides can be formed from a monomer or various monomers (mixed sugars). As polymer carrier molecules in this respect, carrier molecules are suitable which improve the pharmacological properties, such as longer retention time. Polymer carrier molecules with many bound siglec inhibitor ligands enable cross-linking and consequently the activation of the siglec receptor molecules. The application of such polymer carrier molecules therefore enables fine regulation.

The carrier molecules preferably contain a core and various quantities of substances according to the invention which are bound to it through suitable spacers. The desired pharmacological effect can be controlled through the composition of the polymers comprising the core and substances according to the invention. Preferably, the polymers (core) are dendrimers, polyacrylamide or polylactide. The substances according to the invention for example, can be coupled either chemically or enzymatically to the polymers.

According to the invention Z signifies an atom selected from O, N, C or S.

According to the invention R1 is an H atom, a hydroxy group or a derivative of them. Suitable derivatives of the hydroxy group are in this respect an amino or thio group which can be substituted as applicable.

According to the invention R2 signifies a hydroxy or amine group or a derivative of them. The naturally occurring substituent is an amino-acetyl group. Suitable derivatives are, for example, those with which the amino group is substituted by an acetyl, propionyl, butyl or pentyl group. The alkanoyl group can in this respect furthermore be substituted by one or more halogen atoms. Other suitable derivatives can be taken from (Reference 5; compounds 4 to 12). The modification on position R2 can contribute to an increase in the specificity of the siglec inhibitor for a given siglec molecule.

According to the invention R3 signifies a hydroxy group or a derivative of it. In this respect, suitable derivatives are, for example, an amino or thio group which can be substituted where applicable.

According to the invention R4 signifies a hydroxy group or a derivative of it. In this respect, suitable derivatives are groups which act as H acceptors. Examples of derivatives in this respect are an amino or thio group, which can be substituted where applicable, whereby the H acceptor property is retained.

According to the invention R6 and R6' signify independently of one another an H atom or an alkyl group, a charged group or a derivative of them, whereby at least one substituent is selected from R6 and R6' is a hydrophobic group, preferably an H atom or a methyl group. Suitable derivatives are low alkyl substituents such as methyl, ethyl, propyl or butyl groups. Suitable charged groups are, for example, carboxy, sulphate or phosphate groups.

According to the invention R7 signifies an H atom or any group, preferably a group for improving the pharmacological properties of the siglec inhibitor. Groups for improving the pharmacological properties can be polymer carrier molecules. The complete siglec inhibitor should preferably exhibit such a hydrophilicity which leads to an even distribution of the inhibitor in a hydrophilic and hydrophobic phase.

Furthermore, the covalent or non-covalent binding of the siglec inhibitors according to the invention on natural glyco-conjugates and glyco-proteins is taken into consideration.

It was surprisingly found that through the introduction of hydrophobic substituents on the amino group of the 9-amino-9-desoxy-sialic acid, in particular neuraminic acid, siglec inhibitors with increased affinity relative to the reference compound 5'-acetyl-neuraminic acid were obtained. According to preferred embodiments, siglec inhibitors are provided which specifically bind to certain siglec proteins and inhibit them.

According to a preferred embodiment, the alkanoyl group is selected from an ethanoyl, propanoyl, butanoyl, pentanoyl, hexanoyl, heptanoyl, octanoyl, nonanoyl and decanoyl group, preferably hexanoyl. According to the invention branched alkanoyl groups are also taken into consideration.

In a further preferred embodiment the cycloalkanoyl group is selected from a $C_3$ to $C_6$ cycloalkanoyl group, preferably cyclohexanoyl.

In another preferred embodiment the aryl-carbonyl group is selected from a $C_4$ to $C_{15}$ aryl-carbonyl group, preferably from a benzoyl group, naphthoyl group, anthracen-carbonyl group, whereby this residue primarily takes part in the selectivity. The selectivity can be in this way controlled through a suitable selection.

In another preferred embodiment the heteroaryl-carbonyl group is selected from a pyridyl-carbonyl group, chinaldine-carbonyl and thiophenyl-carbonyl group.

In another embodiment the alkyl group is selected from a $C_1$ to $C_{20}$ alkyl group, preferably from a methyl, ethyl, propyl, butyl, pentyl and hexyl group.

According to the invention branched alkyl groups are also considered.

In another preferred embodiment the cycloalkyl group is selected from a $C_3$-$C_6$ alkyl group.

In a further preferred embodiment the aryl group is selected from a phenyl, naphthyl, biphenyl and anthracen group. According to the invention the aryl group can be selected both from condensed as well as non-condensed aryl groups.

The heteroaryl group selected from a pyridyl, chinaldine and thiophenyl group is also preferred.

The heteroaryl group comprises, according to the invention, both condensed and also non-condensed hetero-aromatic systems which are known to the specialist.

A particularly preferred compound is methyl-α-9-N-(naphthyl-2-carbonyl)-amino-9-desoxy-Neu5Ac. This sialic acid derivative binds approximately twelve times stronger to siglec-1 than the reference compound 2-alpha-methyl-5-N-acetyl-neuraminic acid and stronger still to siglec-4a (approx. 236 times stronger).

Methyl-α-9-N-(biphenyl-4-carbonyl)-amino-9-desoxy-Neu5Ac is also particularly preferred. This compound binds approximately 150 times stronger to siglec-2 than the reference compound 2-alpha-methyl-5-N-acetyl-neuraminic acid.

Furthermore, methyl-α-9-N-benzoyl-amino-9-desoxy-Neu5Ac is particularly preferred. This compound binds approximately 704 times stronger to siglec-4a (MAG) than the reference compound 2-alpha-methyl-5-N-acetyl-neuraminic acid.

According to a preferred embodiment of the invention a siglec inhibitor is provided, whereby
   X signifies a carboxy group, which should be present in an axial position;
   Y signifies an H atom, an O-methyl, O-benzyl group or a derivative of a hydroxy group;
   Z signifies an O atom;
   R1 signifies a hydroxy group;
   R2 signifies an amino-acetyl group;
   R3 signifies a hydroxy group;
   R4 signifies a hydroxy group;
   R6 signifies an H atom;
   R6' signifies an H atom; and
   R7 signifies an H atom.

With the exception of Y, the quoted substituents in this respect match the naturally occurring substituents of sialic acid.

The invention also provides a method for the manufacture of siglec inhibitors with increased affinity for a siglec molecule, which includes the steps:
   a) introduction of a substituent selected from the residues according to the invention in the position R5 of neuraminic acid or derivatives of it;
   b) determination of the affinity of the product according to a) for a siglec molecule;
   c) selection of the products with increased affinity;
   d) where applicable, further substitution of the selected product according to c) in positions different from position R5, preferably in position R2.

According to the invention, it was found that siglec inhibitors with increased affinity for a siglec molecule can be obtained by introducing a hydrophobic substituent in position R5 of the neuraminic acid or derivatives of it. The determination of the affinity of the product for a given siglec molecule can in this respect occur by a binding assay or a Hapten inhibition test. The conditions for the Hapten inhibition assay are in this respect, as stated above, preferably as specified in (5, 6). The affinity of the selected products for a given siglec molecule can be further increased by the introduction of substituents in positions different from position R5, preferably position R2. Suitable substituents for R2 are in this respect the substituents stated for R5.

The invention also provides a method for increasing the binding selectivity of siglec inhibitors which includes the step of introducing a substituent selected from the residues for R5 according to the product of the present invention in position R5 of neuraminic acid or derivatives of it.

The synthesis of the compounds according to the invention is in principle possible for the specialist based on his general specialist knowledge. Preferred as the starting product is 5-N-acetyl-neuraminic acid, from which first the appropriate alkyl, aryl, alkyl-alpha-O- or alpha-S-glycosides are produced in a reaction sequence comprising several steps.

The next step consists of replacing the hydroxy group on C9 (R5 according to this invention) of the appropriate O- or S-glycoside of the 5-N-acetyl-neuraminic acid by an amino group. This transformation can be carried out via the appropriate 9-O-tosyl compound. Preferably, this reaction can be carried out using a modified Mitsunobu reaction. The thus obtained alkyl, aryl, aralkyl-alpha-O- or alpha-S-glycosides of the 9-amino-9-desoxy-5-N-acetyl-neuraminic acid finally supply the appropriate alkyl, aryl, alkyl-alpha-O- or alpha-S-glycosides of the 5-N-acetyl-9-(biphenyl-4-carbonyl)-amino-9-desoxy-neuraminic acid and similar substances with a varying acyl residue on the C-9 (R5 according to the invention) constant amino group. The execution of this linkage of acid function with amino group can be carried out in various ways, for example by using the respective acid chloride or anhydride or with the aid of the carbodiimide method or via the method of the respective acid function, activated for example with nitrophenol, pentafluorphenol, etc.

This invention also provides pharmaceutical compositions comprising at least one siglec inhibitor according to the invention and a pharmaceutically compatible carrier. According to a preferred embodiment the therapeutically applicable siglec inhibitors are as selective as possible for a siglec molecule. Pharmaceutically compatible carriers are known to the specialist.

These also include suitable dilution agents. Generally, any form of administering is suitable, e.g. intravenously, intraperitoneally, subcutaneously, intradermally, orally or topically, whereby the oral administration is preferred in this respect.

The amount of medicament to be administered can be determined routinely by the doctor.

Furthermore, this invention provides the application of the siglec inhibitors according to the invention for the treatment of diseases mediated by siglecs, preferably diseases of the immune system. Siglec-2 participates in the regulation of the immune response dependent on B-cells. This invention therefore indicates the application of the siglec inhibitors for the regulation of the immune response dependent on B-cells. In this respect, according to the invention, allergies, auto-immune diseases and chronic inflammations are quoted as subjects for a siglec inhibitor treatment.

Siglec-4a exhibits a neurite growth-inhibiting effect. The siglec inhibitors according to the invention are therefore suitable for neutralizing the neurite growth inhibiting effect of siglec-4a and therefore possess the capability of improving the regeneration capability of damaged nerves, for example in the treatment of paraplegia. Siglec-7 takes part, for example, in the regulation of the cytotoxic activity of NK cells. The sialic acid derivatives according to the invention are therefore suitable for the regulation of the cytotoxic activity of these cells. For example, treatable diseases in this regard are cancer diseases and viral diseases, in particular AIDS.

There are indications of the participation of other siglecs in the control of the immune system, cf. Table 1. The siglec inhibitors according to the invention are therefore also suitable for the control of the immune system.

The preferred siglec inhibitors according to the invention result in an increased immune response dependent on B-cells, which can be verified in particular by an increased $Ca^{2+}$ secretion. This increased $Ca^{2+}$ secretion arises through the application of the preferred siglec inhibitors according to the invention, verifiable, for example, in tests with Daudi cells or B-cells from mice. This increased immune response, dependent on B-cells, induced through the application of the preferred siglec inhibitors of this invention, opens up many promising possibilities for the manufacture of medicaments for the treatment of diseases associated with immune defects. A compound preferred in this connection is methyl-$\alpha$-9-N-(biphenyl-4-carbonoyl)-amino-9-desoxy-Neu5Ac (illustrated in the examples). This compound also shows in particular a very remarkable selective affinity for hCD22. Medical indications for which the preferred inhibitors show special potential are diseases in which the immune response within the scope of the B-cell activation is disturbed. Examples of this are the Common Variable Immunodeficiency (CVID) and the IgA deficiency. CVID patients have B-cells which however cannot initiate an effective immune response and are characterised by a hypogammaglobulinemia. They suffer from severe infectious diseases and can currently only be treated with immune globulins, which however is a problematic therapy with regard to the significant risks and restricted scope of application. Patients with IgA deficiency could also be treated with immune globulins, which though is often not undertaken due to the risks described above and also because these patients often only exhibit slight symptoms.

In the following, examples are described which explain the invention, but which should not restrict it. When making use of the invention, other applications will open up for the specialist which are also included according to the invention.

Materials and Methods

Synthesis of Siglec Inhibitors

As an example of the production of the above quoted substances acylated on the amino group of the methyl-$\alpha$-5-N-acetyl-9-amino-9-desoxy neuraminic acid, the synthesis of the methyl-$\alpha$-5-N-acetyl-9-N-(biphenyl-4-carbonyl)-amino-9-desoxy-neuraminic acid (3) is described here.

Methyl-$\alpha$-5-N-acetyl-9-azido-9-desoxy-neuraminic acid (1)

a) From methyl-$\alpha$-5-N-acetyl-9-O-tosyl-neuraminic acid methyl ester, according to methods known from publications, via the appropriate 9-azide and saponification of the ester group.
b) Direct from known methyl-$\alpha$-N-acetyl-neuraminic acid through chemical reaction based on the Mitsunobu reaction.

A solution of the triethyl-ammonium salt of the methyl-$\alpha$-5-N-acetyl-neuraminic acid (0.1 g) in dry pyridine (0.4 ml) and N,N-dimethyl-formamide (DMF) (1 ml) is concentrated in a vacuum and then fumed with dried DMF 1-2 times (A).

Tetramethylguanidine (0.19 g) is dissolved in a mixture of dry pyridine (0.25 ml) and DMF (1 ml), the solution is concentrated in a vacuum and then fumed with dry DMF 1-2 times (B). A is dissolved in DMF (0.8 ml), the solution added to B and 98-100% formic acid (0.13 ml) is added. The solution of A+B is added to a mixture of triphenylphosphine (0.17 g) and diisopropylazodicarboxylate (0.125 ml) in dried tetrahydrofurane (1.2 ml), which first was incubated at 0° C. for about 15 minutes. After about 24 hours at 0° C.→20° C. the reaction is terminated and about 0.5 ml of methanol are then added. The solution is concentrated in a vacuum, shaken out with ethyl acetate/$H_2O$ or methylene chloride/$H_2O$ and chromatographed on silica gel (Flash method).

Elution: First methanol/ethyl acetate/acetic acid (20%) 1/6/1, then 1/4/1.

Yield: 70-80% of theory.

Methyl-α-5-N-acetyl-9-amino-9-desoxy-neuraminic acid (2)

The 9-azido compound (1) is hydrogenated with palladium oxide in $H_2O$ at normal pressure.

Yield: 95%.

Methyl-α-5-N-acetyl-9-N(biphenyl-4-carbonyl)-amino-9-desoxy-neuraminic acid (3)

Chemical reaction of biphenyl-4-carboxylic acid (0.4 g) with 4-nitrophenol (0.28 g) in ethyl-acetate in the presence of N,N'-dicyclohexyl-carbodiimide (0.416 g) at room temperature yields respective biphenyl (4)-carboxylic acid 4-nitrophenylester, which crystallises from ethyl acetate/diethyl ester/hexane.

Methyl-α-5-N-acetyl-9-amino-9-desoxy-neuraminic acid (2) (30 mg) dissolved in dried DMF (0.6 ml) reacts in the presence of triethylamine (12.9 ml) completely with the above quoted nitrophenylester (39 mg) at room temperature. Purification occurs through chromatography on silica gel (Flash method).

Elution: First methanol/ethyl acetate/acetic acid (20%) 1/6/1, then 1/5/1, finally 1/4/1.

Yield of (3): 93%.

High resolution NMR spectroscopy and FAB-MS show the structure of the synthesised products.

Hapten Inhibition Assay

The Hapten inhibition assay is carried out under the conditions quoted in (5, 6).

Results

TABLE 2

| Structure | Siglec-4a (MAG) IC50 | rIP | Siglec-1 (sialoadhesin) IC50 | rIP | Siglec-2 (human CD22) IC50 | rIP | Siglec-2 (murine CD22) IC50 | rIP |
|---|---|---|---|---|---|---|---|---|
| Methyl-α-Neu5Ac | 4716 | 1.0 | 884 | 1.0 | 1388 | 1.0 | 4689 | 1.0 |
| Methylthio-α-Neu5Ac | 2775 | 1.3 | 600 | 0.8 | 1367 | 1.6 | 4250 | 1.1 |
| Benzylthio-α-Neu5Ac | 2000 | 3.0 | 280 | 4.1 | n. d. | n. d. | n. d. | n. d. |
| 2,3-sialyllactose | 1600 | 7.3 | 385 | 2.4 | n. d. | n. d. | n. d. | n. d. |
| Methyl-α-5-N-glycolyl-neuraminic acid | n. d. | n. d. | n. d. | n. d. | 1013 | 1.0 | 703 | 8.3 |
| Methyl-α-methyl-α-5-N-fluoracetyl-neuraminic acid | 280 | 17.1 | 625 | 1.9 | n. d. | n. d. | n. d. | n. d. |
| Methyl-α-methyl-α-5-N-fluoracetylaminoacetyl-neuraminic acid | >>10 mM (90%) | n. a. | 2500 | 0.4 | n. d. | n. d. | n. d. | n. d. |
| Benzyl-α-5-N-propanoyl-neuraminic acid | 2500 | 4.8 | 215 | 3.4 | n. d. | n. d. | n. d. | n. d. |
| Benzyl-α-5-N-butanoyl-neuraminic acid | 5300 | 1.5 | 250 | 2.7 | n. d. | n. d. | n. d. | n. d. |
| Benzyl-α-5-N-benzoyl-neuraminic acid | <10 mM (27%) | >0.27 | >10 mM (63%) | <0.05 | n. d. | n. d. | n. d. | n. d. |
| Methyl-α-ketodesoxy-nonulsonic acid (KDN) | >>1.0 mM (225%) | <<0.5 | >1 mM (74%) | <0.8 | >>1 mM (117%) | <<2 | >2 mM (74%) | <1.5 |
| Methyl-α-5-N-(etoxycylcobutendion)-neuraminic acid | 4300 | 0.5 | >>5 mM (92%) | <<0.15 | 940 | 2.3 | 3367 | 1.5 |
| Methyl-α-9-methylsulphoxido-9-desoxy-Neu5Ac | 697 | 8.5 | 2000 | <0.05 | n. d. | n. d. | n. d. | n. d. |
| Methyl-α-9-methylthio-9-desoxy-Neu5Ac | >10 mM (116%) | <<0.27 | 5000 | <<0.05 | n. d. | n. d. | n. d. | n. d. |
| Methyl-α-9-methylsulphonyl-9-desoxy-Neu5Ac | 3400 | 0.1 | 2000 | <<0.05 | n. d. | n. d. | n. d. | n. d. |
| Methyl-α-9-N-aminoacetyl-9-desoxy-Neu5Ac | 3400 | 3.3 | 7480 | 0.3 | n. d. | n. d. | n. d. | n. d. |
| Methyl-α-9-N-oxamido-amino-9-desoxy-Neu5Ac | n. d. | n. d. | >4000 (57%) | <0.2 | n. d. | n. d. | n. d. | n. d. |
| Methyl-α-9-carboxy-Neu5Ac | >>1000 (87%) | <<2.4 | >4000 (63%) | <0.2 | n. d. | n. d. | n. d. | n. d. |
| Methyl-α-9-N-acetyl-amino-9-desoxy-Neu5Ac | 2150 | 3.7 | 3817 | 0.2 | 1800 | 0.6 | 1.750 | 2.7 |
| Methyl-α-9-N-trifluoracetyl-amino-9-desoxy-Neu5Ac | 550 | 10 | 4000 | 0.5 | n. d. | n. d. | n. d. | n. d. |
| Methyl-α-9-N-thioacetyl-amino-9-desoxy-Neu5Ac | 733 | 6.5 | 6000 | 0.3 | n. d. | n. d. | n. d. | n. d. |
| Methyl-α-9-N-acetoacetyl-amino-9-desoxy-Neu5Ac | 1007 | 6.2 | >10 mM (62%) | <0.05 | n. d. | n. d. | n. d. | n. d. |
| Methyl-α-9-N-hexanoyl-amino-9-desoxy-Neu5Ac | 198 | 54 | 1458 | 0.7 | n. d. | n. d. | n. d. | n. d. |

TABLE 2-continued

| Structure | Siglec-4a (MAG) IC50 | rIP | Siglec-1 (sialo-adhesin) IC50 | rIP | Siglec-2 (human CD22) IC50 | rIP | Siglec-2 (murine CD22) IC50 | rIP |
|---|---|---|---|---|---|---|---|---|
| Methyl-α-9-N-cyclohexanoyl-amino-9-desoxy-Neu5Ac | 110 | 50 | >>1 mM (93%) | 0.2 | 383 | 4.1 | 760 | 6.9 |
| Methyl-α-9-N-(2,3-diacetylaminopropanoyl)-amino-9-desoxy-Neu5Ac | 2500 | 2.3 | >>10 mM (80%) | <<0.1 | n. d. | n. d. | n. d. | n. d. |
| Methyl-α-9-N-(gly)$_2$-amino-9-desoxy-Neu5Ac | 5000 | 0.9 | >>10 mM (100%) | <<0.1 | n. d. | n. d. | n. d. | n. d. |
| Methyl-α-9-N-(gly)$_3$-amino-9-desoxy-Neu5Ac | >10 mM (88%) | <<0.27 | <<10 mM (11%) | >>0.05 | n. d. | n. d. | n. d. | n. d. |
| Methyl-α-9-N-(ethoxycyclobutendion)-amino-9-desoxy-Neu5Ac | 240 | 32 | 1333 | 0.2 | n. d. | n. d. | n. d. | n. d. |
| Methyl-α-9-N-(pyridine-3-carbonyl)-amino-9-desoxy-Neu5Ac | 25 | 170 | 4000 | 0.5 | 445 | 2.3 | 335 | 14 |
| Methyl-α-9-N-benzoyl-amino-9-desoxy-Neu5Ac | 7 | 704 | 539 | 1.8 | 290 | 5.7 | 1094 | 3.7 |
| Methyl-α-9-N-(3,5-dihydroxybenzoyl)-amino-9-desoxy-Neu5Ac | 28 | 166 | 525 | 1.7 | 73 | 19 | 1467 | n. d. |
| Methyl-α-9-N-(acetamidobenzoyl)-amino-9-desoxy-Neu5Ac | 62 | 77 | 295 | 3.0 | 580 | 2.4 | 1033 | n. d. |
| Methyl-α-9-N-(phenylacetyl)-amino-9-desoxy-Neu5Ac | 367 | 7 | n. d. | n. d. | n. d. | n. d. | n. d. | n. d. |
| Methyl-α-9-N-(2,4-dinitrobenzoyl)-amino-9-desoxy-Neu5Ac | 205 | 18 | 733 | 0.3 | 287 | 7.7 | 593 | 7.9 |
| Methyl-α-9-N-(4-methoxybenzoyl)-amino-9-desoxy-Neu5Ac | 12 | 393 | 42 | 8.4 | 120 | 19 | 667 | 7.4 |
| Methyl-α-9-N-(pentafluorbenzoyl)-amino-9-desoxy-Neu5Ac | 107 | 42 | 7000 | 0.3 | 360 | 3.3 | 2500 | 2.0 |
| Methyl-α-9-N-(biphenyl-4-carbonyl)-amino-9-desoxy-Neu5Ac | 22 | 218 | 52 | 13 | 4 | 150 | 1220 | 5.0 |
| Methyl-α-9-N-(biphenyl-4-acetyl)-amino-9-desoxy-Neu5Ac | n. d. | n. d. | 3000 | 0.3 | 35 | 29 | 123 | 48 |
| Methyl-α-9-N-(biphenyl-2-carbonyl)-amino-9-desoxy-Neu5Ac | n. d. | n. d. | 2600 | 0.3 | 97 | 10 | 647 | 9.5 |
| Methyl-α-9-N-(phenoxy-3-benzoyl)-amino-9-desoxy-Neu5Ac | n. d. | n. d. | 540 | 1.5 | 10 | 111 | 887 | 6.7 |
| Methyl-α-9-N-(diphenyl acetyl)-amino-9-desoxy-Neu5Ac | 150 | 31 | 4400 | 0.2 | 35 | n. d. | 103 | n. d. |
| Methyl-α-9-N-(naphthyl-2-carbonyl)-amino-9-desoxy-Neu5Ac | 20 | 236 | 78 | 12 | 6 | 167 | 270 | 18 |
| Methyl-α-9-N-(naphthyl-1-carbonyl)-amino-9-desoxy-Neu5Ac | 56 | 84 | 3000 | 0.3 | 37 | 27 | 92 | 64 |
| Methyl-α-9-N-(naphthyl-2-acetyl)-amino-9-desoxy-Neu5Ac | 367 | 13 | 1750 | 0.5 | 8 | 131 | 71 | 83 |
| Methyl-α-9-N-(anthracen-5-carbonyl)-amino-9-desoxy-Neu5Ac | 162 | 28 | 750 | 0.5 | 338 | 4.9 | 647 | 7.4 |
| Methyl-α-9-N-(cyclobutendion)-amino-9-desoxy-Neu5Ac | n. d. | n. d. | n. d. | n. d. | 180 | 5.7 | 620 | 7.4 |
| Methyl-α-9-N-(chinaldine-2-carbonyl)-amino-9-desoxy-Neu5Ac | 87 | 54 | >>2.5 mM (100%) | <<0.2 | 41 | n. d. | >>10 mM (100%) | n. d. |
| Methyl-α-9-N-dansyl-amino-9-desoxy-Neu5Ac | 317 | 19 | 260 | 2.6 | n. d. | n. d. | n. d. | n. d. |
| Methyl-α-9-N-fluoresceinyl-amino-9-desoxy-Neu5Ac | 106 | 41 | >>1.5 mM (121%) | <<0.5 | 77 | 28 | 100 | 48 | gly = glycine

The IC50 value is the siglec inhibitor concentration which leads to 50% inhibition in the binding in the Hapten inhibition assay. The rIP value of each sialic acid derivative was determined by forming the quotient of the IC50 value of the comparative compound 5-N-acetyl-neuraminic acid and of the IC50 value of the compound to be investigated. Sialic acid derivatives with an rIP value of >1.0 therefore bind better than the reference compound and an rIP value of <1 shows that the compound binds worse to the receptor than the reference compound. n.d. signifies that no determination had been conducted.

The compound BPC-Neu5Ac (shown below) was used according to known methods in test series for the investigation of the selectivity and the activity. The stimulation of Daudi cells with anti-IgM in the presence of BPC-Neu5Ac produced a rise in the $Ca^{2+}$ concentration. The application of this compound also led to a clearly increased $Ca^{2+}$ concentration in primary B-lymphocytes from human blood which were stimulated with anti-IgM. This data indicates that the increased $Ca^{2+}$ signal of the treated cells is caused by a specific inhibition of the ligand binding domain of CD22. This impairment with regard to the binding of ligands leads to an incomplete activation of the intracellular inhibitor domain of CD22.

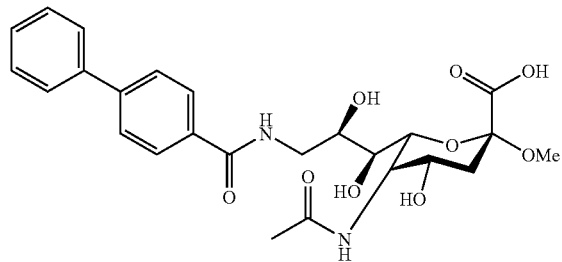

Methyl-α-9-N-(biphenyl-4-carbonyl)-amino-9-desoxy-Neu5Ac (BPC-Neu5Ac)

REFERENCES

1) Crocker et al., Immunology 102 (2001), 1-14.
2) Crocker et al., (2000) The siglec family of I-type lectins in Carbohydrates in Chemistry and Biology, Vol. 4, B. Ernst et al., publisher, Wiley-VCH, pp. 579-595.
3) Kelm, S. (2001), Ligands for siglecs. In Mammalian Carbohydrate Recognition Systems, P. R. Crocker, publisher (Berlin, Springer), pp. 153-176.
4) May et al., Mol. Cell 1 (1998), 719-728.
5) Kelm et al., Eur. J. Biochem. 255 (1998), 663-672.
6) Strange et al., Eur. J. Biochem. 258 (1998), 677-685.
7) Li, N. et al., Cloning and Characterization of Siglec-11, a novel sialic acid binding member of the Ig Superfamily from human dendritic cells; J. Biol. Chemistry 2001 (in printing).
8) Crocker et al., Glycobiology 8 (1998), v.

The invention claimed is:

1. A method of increasing the binding selectivity of siglec inhibitors comprising introducing at the C-9 position of neuraminic acid a substituted or unsubstituted amino group, whereby the substituent is selected from the group consisting of substituted or unsubstituted formyl, alkanoyl, cycloalkanoyl, aryl-carbonyl, alkyl, aryl, and cycloalkyl groups, wherein these groups can also include one or more unsaturated bonds, and wherein the neuraminic acid has the following formula:

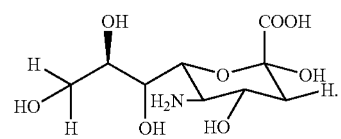

2. A method for producing siglec inhibitors with increased affinity for a siglec molecule comprising:

a) replacing the hydroxyl group at the C-9 position of neuraminic acid with a substituted or unsubstituted amino group, whereby the substituent is selected from the group consisting of substituted or unsubstituted formyl, alkanoyl, cycloalkanoyl, aryl-carbonyl, alkyl, aryl, and cycloalkyl groups, wherein these groups can also include one or more unsaturated bonds;
b) determining the affinity of the product according to a) for a siglec molecule;
c) selecting the products with increased affinity; and
d) optionally, further substituting the amino group at position C-5 of the product of step c).

* * * * *